(12) United States Patent
Wang

(10) Patent No.: US 8,945,585 B2
(45) Date of Patent: Feb. 3, 2015

(54) **MULTI-TARGET RECOMBINATION GENE AND THE APPLICATION OF ITS PROTEIN TO PREVENT AND CURE *HELICOBACTER PYLORI***

(75) Inventor: Baoning Wang, Chengdu (CN)

(73) Assignee: Sichuan Vaccine Technology Co., Ltd., Chengdu, Sichuan Province (CN)

( * ) Notice: Subject to any disclaimer, the term of this patent is extended or adjusted under 35 U.S.C. 154(b) by 0 days.

(21) Appl. No.: 13/516,733

(22) PCT Filed: Aug. 29, 2011

(86) PCT No.: PCT/CN2011/079042
§ 371 (c)(1),
(2), (4) Date: Jun. 17, 2012

(87) PCT Pub. No.: WO2012/031530
PCT Pub. Date: Mar. 15, 2012

(65) Prior Publication Data
US 2014/0112948 A1    Apr. 24, 2014

(30) Foreign Application Priority Data

Sep. 7, 2010 (CN) .......................... 2010 1 0274782

(51) Int. Cl.
*A61K 39/02* (2006.01)
*A61K 39/00* (2006.01)
*C07H 21/04* (2006.01)
*C07K 14/205* (2006.01)
*C07K 14/245* (2006.01)

(52) U.S. Cl.
CPC .............. *C07K 14/205* (2013.01); *A61K 39/02* (2013.01); *A61K 39/105* (2013.01); *C07K 14/245* (2013.01); *C07K 2319/00* (2013.01)
USPC ....... 424/234.1; 424/9.1; 424/9.2; 424/184.1; 424/185.1; 536/23.1; 536/23.7

(58) Field of Classification Search
CPC ....... A61K 49/00; A61K 39/00; A61K 39/38; A61K 39/02; A61K 39/0208; A61K 38/04; C07H 21/02; C07H 21/04
USPC .................. 424/9.1, 9.2, 184.1, 185.1, 234.1; 536/23.1, 23.7
See application file for complete search history.

*Primary Examiner* — Rodney P Swartz

(57) ABSTRACT

The present invention discloses a multi-target recombination gene and the application of its protein to prevent and cure *Helicobacter pylori*. It includes a multi-target fusion polypeptide having amino acid sequence shown in SEQ ID NO:2, a multi-target recombination gene of encoding multi-target fusion polypeptide having nucleotide sequence shown in SEQ ID NO:1, and the application of the multi-target recombination gene or the multi-target fusion polypeptide or specific antibody of the multi-target fusion polypeptide as biological products for preventing and curing *Helicobacter pylori*. The present invention effectively combines the key target protein UreI for Hp gastric colonization, and antigen target of UreB to create the best drug target.

3 Claims, 3 Drawing Sheets

MULTI-TARGET RECOMBINATION GENE AND THE APPLICATION OF ITS PROTEIN TO PREVENT AND CURE *HELICOBACTER PYLORI*

BACKGROUND OF THE PRESENT INVENTION

1. Field of Invention

The present invention relates to biotechnology, more particularly to a multi-target recombination gene and the application of its protein to prevent and cure *Helicobacter pylori*.

2. Description of Related Arts

*Helicobacter pylori* (Hp) is an important pathogenic bacteria that was found in 1982. The study shows that this bacteria can not only cause gastritis and gastric ulcer, but also is closely relevant to the MALT lymphoma and gastric cancer. This bacteria is the only bacterial pathogens that is relevant to the human tumor announced by WHO. The recent study also discovers that the Hp is also closely relevant to the cardiovascular disease such as coronary disease. Hp can infect seniors, children and young adults, but the infection rate differs a lot in different countries and regions and differs according to different economic levels and living habits. The infection rate is about 50-80% among the general population in China, and it is increasing by 1-2% each year.

The urease gene of Hp was cloned in 1989, and the complete genome sequence of Hp was determined in 1997. Agnes etc analyze the urease by utilizing the shuttle clone technology, and confirm that a group of genes of encoding urease is located in the 4.2 kb DNA fragment, and there are 4 open reading frames (ORF), which are named ureA, ureB, ureC and ureD respectively. Further study shows that the ORF of ureC and ureD next to the ureA and ureB are ureI, ureE, ureF, ureG and ureH respectively. The length of the entire urease gene is 8 kb. In 1998, Stéphane of Institute Pasteur believes that the ureI gene is irrelevant to the urease of Hp, but is closely relevant to the gastric colonization, and is the necessary gene to the gastric colonization of Hp. In 2000, Rektorschek did comparative study by using genetic mutation technique and pointed that the ureI encodes the urea membrane channel protein of Hp. UreI gene transforms to 6 fragments of transmembrane protein UreI via in vitro transcription and translation. The protein is independent to the cell membrane of Hp, and protects the urease activity in the stomach acid environment where pH is lower than 4. The experiment shows that the intracellular urease can maintain activity without ureI protein when pH is higher than 4, but ureI is necessary gene to maintain urease activity when pH is lower than 4. In 2001, David L. Weeks believes that the UreI is the important channel protein for Hp to connect with the urease and gastric colonization. UreI has key function to the gastric colonization of Hp. There is a research that uses *Xenopus oocytes* as transgenic cell model to observe that the expression of ureI can promote the absorption of urea in an acid environment. However, the ureI mutant where the periplasmic histidine 123 is missing can not promote the absorption of urea. In the mean time, the urea transportation mediated by ureI is urea specific, passive, unsaturated and nonpolar, and non temperature-dependent. Weeks pointed out that the ureI is the H+ controlled urea channel of Hp, adjusts and controls the metabolism of intracellular urease, and is very important to the gastric colonization and survival of Hp. David R. Scott's study suggests that, with urea, ureI can stimulate the production of intracellular ammonia, but replacing urea with acetamide does not have the same result. Therefore, the function that ureI assists urease to resolve urea is specific. Furthermore, study also shows that UreI has four conservative histidine residues (H71, H123, H131, H193); three intracellular polypeptide rings has conservative zones (G166, K167, F168); the far end H193 (not H123) plays a decisive role for Hp to produce ammonia in the low pH environment; the third intracellular ring of UreI is important to the membrane channel activity of UreI. These illustrate the new molecule mechanism of gastric colonization of Hp.

A great amount of studies and clinical treatment experiment show that the infection and colonization of Hp is the primary cause of pathogenicity. When Hp is cleared, Gastritis and Gastric Ulcer get better. The pH value of human gastric mucosa from 2 to 4, and the pH value of gastric juice is around 2. Weeks' study shows that the extracellular urease of Hp is inactive when pH value is no more than 4.5, and can survive no more than 5 minutes when pH value is lower than 4.0. So why can Hp survive in the high acid environment of the stomach? Weeks and Scott believe that the urea channel UreI of Hp can take urea from outside of cell for intracellular urease to be resolved into NH3 and CO2. The ammonia cloud formed by the NH3 creates a cozy environment of hypoxia and weak acid for colonization, which becomes the necessary molecule for Hp colonization. However, there is no further report on the immunological characteristics of UreI molecule and whether it can be served as drug target to avoid Hp infection.

In 2000, Scott etc found that UreI is important to the activation of intracellular urease of Hp in the acid environment. In 2001, Week etc discovered that UreI is very important to the gastric colonization and pathogenicity of Hp through genetic mutation research. Skouloubris verified that UreI is irrelevant to the activity of urease via gene silencing technology such as RNAi, but is necessary to the colonization and proliferation of Hp in low pH value environment. In 2002, Mollenhauer proved that UreI is important to the colonization and the survival after colonization of Hp via experiment on Gerbillinae.

In 1998, Skouloubris etc verified that UreB is a subunit of urease activity, and is a necessary gene for colonization and proliferation of Hp in low pH value environment. In 2009, oral recombination *Helicobacter pylori* vaccine, whose main components is recombination UreB protein, is approved by the Chinese State Food and Drug Administration for first class new drug in April 2009, and enters stage of industrialization and clinical expansion and application. Though UreB is the acknowledged target of Hp vaccine, because of its many drawbacks, such as single gene target, prokaryotic expression, preparation purification, renaturation preservation, combine immunodominant antigen epitope in series so as to form multi-target recombination gene, which can be served as muti-target DNA vaccine and its corresponding recombinant protein vaccine or specific antibody product for preventing and curing Hp. Currently, there is still no report on biopharmacy medicine research of multi-target recombination gene and its protein for preventing and curing Hp.

Currently, from the current situation of Hp clinical treatment, the routine treatment for Hp infection is to use antibiotics or combined with antibiotics. However, though this broad-spectrum antibiotics treatment plays a certain role for removing Hp, this treatment may easily causes flora disorder and produces drug resistant strain, and is against the prevention and cure of Hp in the stomach and natural environment. Proton Pump Inhibitor (PPI) treatment can inhibit gastric acid secretion, but with the rebound of HP value in stomach, it creates a neutral environment for Hp colonization, and works to the advantage of Hp number increasing.

From the molecular interaction and biochemical mechanism related to Hp physiological metabolism, block the urea membrane channel by utilizing immune technique so as to block the biochemical reaction of urease resolving urea, and use Hp urease B subunit as target to make the intracellular and extracellular activity of resolving urea disappear at the same time, so that the Hp cannot survive and colonize in the gastric environment. The multi-target combination design by utilizing key molecule of Hp colonization can prevent and cure Hp infection and avoid the drawback of the antibiotics and PPI reagent in the clinical treatment. This biotechnology of polygene and multi-target immunodominant antigen epitope combination is the ideal way to prevent and cure Hp.

SUMMARY OF THE PRESENT INVENTION

An object of the present invention is to provide a multi-target fusion polypeptide having amino acid sequence shown in SEQ ID NO:2, a multi-target recombination gene of encoding multi-target fusion polypeptide having nucleotide sequence shown in SEQ ID NO:1, and the application of the multi-target recombination gene or the multi-target fusion polypeptide or specific antibody of the multi-target fusion polypeptide as biological products for preventing and curing *Helicobacter pylori*.

In order to accomplish the above object, the present invention provides a multi-target fusion polypeptide or its derivatives having amino acid sequence shown in SEQ ID NO:2.

The multi-target fusion polypeptide is derived from fusion of B cell & T cell epitope peptide of Hp urea membrane channel gene and Hp urease B subunit. The multi-target fusion polypeptide can be prepared by prokaryotic or eukaryotic expression or chemical synthesis. The multi-target fusion polypeptide is screened, optimized and spliced by referring to amino acid sequence of Hp urea membrane channel gene (UreI) and urease B subunit (UreB), and their B cell & T cell antigenic epitope via bioinformatics prediction. Experiment proves that it can strongly stimulate the humoral immune response and cellular immune response of human being and animal.

The nucleotide sequence of the amino acid sequence shown in SEQ ID NO:2 is multi-target recombination gene of the nucleotide sequence shown in SEQ ID NO:1, or a nucleotide sequence having variation or replacement of individual base on the basis of sequence shown in SEQ ID NO:1 and having same encoding with SEQ ID NO:1.

The nucleotide sequence shown in SEQ ID NO:1 is obtained by the recombination of nucleotide sequences corresponding to B cell & T cell epitope peptide of Hp urea membrane channel gene and Hp urease B subunit. The recombination sequence is prepared by PCR or synthesis method. The multi-target fusion polypeptide encoded by this nucleotide sequence can strongly stimulate the humoral immune response and cellular immune response of human being and animal.

The present invention also provides a prokaryotic expression vector or eukaryotic expression vector including the nucleotide sequence shown in SEQ ID NO:1.

A multi-target DNA vaccine is the eukaryotic expression vector including the nucleotide sequence shown in SEQ ID NO:1, and the application of the eukaryotic expression vector to biological products for preventing or curing Hp infection.

A multi-target fusion polypeptide vaccine is the application of multi-target fusion polypeptide comprising amino acid sequence shown in SEQ ID NO:2 to biological products for preventing or curing Hp infection.

A antibody product is specific antibody of multi-target fusion polypeptide epitope comprising amino acid sequence shown in SEQ ID NO:2, and is the application of the specific antibody to biological products for preventing or curing Hp infection.

The present invention predicts the Hp ureI and ureB gene and encoding protein and analyzes the antigen epitope, and selectively combines them into a multi-target fusion polypeptide encoding nucleotide sequence that may induce organism to produce immune response. After prokaryotic expression and purification, the tests, such as serum titer and Westernblot test on immunized animals by multi-target fusion polypeptide, serum neutralization test, and CD4+ lymphocyte proliferation prove that the multi-target fusion polypeptide can prevent and cure Hp infection. The details are illustrated as below.

On the first aspect, the present invention provides multi-target fusion polypeptide components from B cell & T cell epitope peptide of Hp urea membrane channel gene and Hp urease B subunit, having amino acid sequence shown in SEQ ID NO:2 or its derivatives.

1: Prepare it based on amino acid sequence shown in SEQ ID NO:2.

2: Obtain amino acid sequence shown in SEQ ID NO:2 via synthesis method or obtain nucleotide sequence or its derivatives shown in SEQ ID NO:1 via PCR method, and digest and connect this gene to prokaryotic expression vector or eukaryotic expression vector, such as PET22b(+) or pIRES2-DsRed2, or other types of expression vector; transform and recombine the expression vector into host strain, such as Rosseta gami II, BL21, or yeast, and construct gene expression engineering bacteria; or clone the nucleotide sequence shown in SEQ ID NO:1 to plant expression vector to express the multi-target fusion polypeptide having amino acid sequence shown in SEQ ID NO:2.

3: Induced expression: obtain multi-target fusion polypeptide having more than 90% purity of SDS-PAGE via various medium purification.

4: The multi-target fusion polypeptide can be prepared to all kinds of biological products, such as vaccine, diagnostic reagent or health products.

On the second aspect, the present invention provides a multi-target DNA vaccine for preventing and curing Hp infection. The multi-target DNA vaccine has nucleotide sequence shown in SEQ ID NO:1 or various nucleic acid preparation derived from this sequence. The preparation method of this DNA vaccine is that: obtain nucleotide sequence or it derivatives having nucleotide sequence shown in SEQ ID NO:1 via synthesis or PCR method, digest and connect it to eukaryotic expression vector, such as pCDNA or various virus vector to prepare various nucleic acid preparation.

On the third aspect, the present invention provides a antibody preparation for preventing and curing Hp infection.

1: This antibody is characterized in having monoclonal or polyclonal antibody that is anti multi-target fusion polypeptide having amino acid sequence shown in SEQ ID NO:2.

2: This antibody can be prepared by immunizing various experimental animals by using multi-target fusion polypeptide having amino acid sequence shown in SEQ ID NO:2, such as preparing monoclonal or polyclonal antibody by using chicken, cattle or laboratory rat.

3: This antibody can be purified via salting out or affinity purification method, or can be directly prepared to all kinds of biological products, such as therapeutic antibody, diagnostic reagent or health products.

The beneficial effect of the present invention is that: effectively combine the key target protein UreI for Hp gastric colonization, and antigen target of UreB to create the best drug target. Obtaining multi-target fusion polypeptide by predicting the immunodominance epitope of ureI and ureB via bioinformatics method not only has significant value to the Hp pathogenesis research, but also to the research of the Hp prevention and therapy reagents. The obtained multi-target fusion polypeptide, DNA vaccine and antibody product show good Hp prevention and curing results on in vitro experiments and animal experiment. Therefore, the present invention has good application prospect.

These and other objectives, features, and advantages of the present invention will become apparent from the following detailed description, the accompanying drawings, and the appended claims.

DETAILED DESCRIPTION OF THE PREFERRED EMBODIMENT

The present invention is further explained in detail with accompanying embodiments and drawings, but the present invention is not limited to these embodiments.

Embodiment 1

The Prediction and Synthesis of Multi-Target Fusion Polypeptide (UreI and UreB Epitope Peptide Look for the amino acid sequence of UreI and UreB in the NCBI protein database, and analyze the B & T cell immunodominant antigen epitope of the two target sequences at same time via online prediction software and DNAstar software. During the experiment, name the nucleotide sequence corresponding to the amino acid sequence having B & T cell immunodominant antigen epitope of UreI and UreB as UreI-B, that is the DNA sequence shown in SEQ ID NO:1; name the amino acid as UreI-B, that is the amino acid sequence shown in SEQ ID NO:2.

The online prediction websites are listed below.
www.imtech.res.in/raghava/propred
http://www.imtech.res.in/raghava/propred
www.epipredict.de/index.html
It is not limited to the above listed websites.

Embodiment 2

The Design and Construction of Multi-Target Fusion Polypeptide DNA Vaccine

Figure 1:
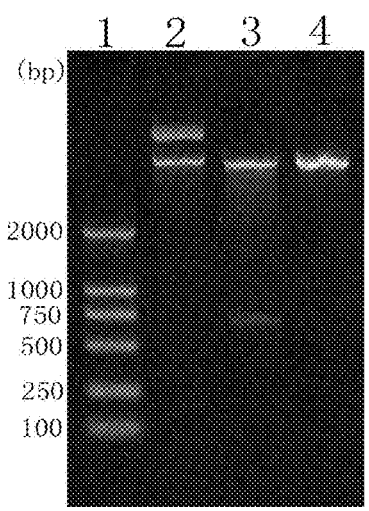
FIG. 1 is an illustrative view of double enzyme digestion of eukaryotic expression vector.

Select pIRES2-DsRed2 as DNA vaccine vector, and connect the DNA sequence of the encoding multi-target fusion polypeptide synthesized in embodiment 1 and the vector after NheI and KpnI double enzyme digestion and transform into competent cell of DH5a. The result of double enzyme digestion is shown in FIG. 1, through positive clone plasmid concentration after PCR and double enzyme digestion preparing transfection cells.

Swim lane 1: DNA MARKER DL2000;
Swim lane 2: pIRES2-DsRed2-ureI-B recombinant plasmid;
Swim lane 3: recombinant plasmid NheI and KpnI double enzyme digestion;
Swim lane 4: pIRES2-DsRed2 empty vector NheI and KpnI double enzyme digestion;
The result shows: pIRES2-DsRed2-ureI-B recombinant plasmid has gene fragment having same size with the predicted multi-target nucleotide sequence.

Embodiment 3

The Transfection of DNA Vaccine of Embodiment 2, Transfection Rate and Expression Verification 3.1 Transfection Process of 293T Cell and Mouse Muscle Primary Cell
(1) HEK293T cells preparation
Digest HEK293T cell with pancreatin and count. Inoculate the cells on the 6-hole board with $1 \times 10^5$/hole, add 2 ml basal medium containing 10% bovine serum, and put it into incubator of 37° C. and 5% $CO_2$. The transfection can be done until the cells grow to have 60~80% density (about 24 h).
(2) mouse muscle cells preparation
Take limb skeletal muscle of 7-day old BALB/c mouse in germ free environment, remove the tendon, and cut it into small pieces. After digest it with 0.125% pancreatin, filter with gauze element, add DMEM medium containing 20% bovine serum, and put it into incubator of 37° C. and 5% $CO_2$ for 48 h for further usage.
(3) preparation for liposome transfection plasmid
Liquid A: mix 25 μg plasmid and 375 μl culture medium without serum evenly.
Liquid B: mix 12 μl Polyfect Transfection and 375 μl culture medium without serum evenly.
(4) Let them stand for 5 minutes at room temperature. Mix the liquid A and liquid B and let it stand at room temperature for 20 minutes.
(5) Wash the cells in 6-hole board with 2 ml culture medium without serum.
(6) Add 750 μl RPMI1640 culture medium without serum to liposome-DNA complex in each tube, mix well, and blow and beat repeatedly by using suction head to completely cover it to the washed cells.
(7) Put it into incubator to cultivate for 5 h.
(8) Add 1.5 ml RPMI1640 with 20% serum, and continue to cultivate. Continue to cultivate transfection cells for 18-24 h, and change to complete 1640 medium (10% bovine serum, 1640 having 100 U/ml penicillin G and 100 μg/ml streptomycin). After 48 h, observe the red fluorescence of cells with fluorescence microscope.

3.2 Recombinant Plasmid Transfection Rate and Expression Verification
(1) Recombinant Plasmid Transfection Efficiency Verification
After HEK293T cell and skeletal muscle cell are transfected for 48 h and 72 h respectively by recombinant plasmid pIRES2-DsRed2, pIRES2-DsRed2-ureI and pIRES2-DsRed2-ctB-ureI, observe the expression of red fluorescence protein under the fluorescence inverted microscope. From the proportion of fluorescence and non-fluorescence cells, the transfection rate is about 80%.

(2) Recombinant Plasmid Intracellular Expression Verification

After transfection for 72 hours, wash it by using 0.01M PBS (PH7.2) for 3 times, fix cell by using 4% paraformaldehyde for 20 minutes at room temperature; after wash it by using PBS, seal it by using 500 μl normal goat serum for overnight; first antibody is prepared by using 500 μl human Hp Positive antibody (1:500) respectively for 2 hours at 37° C.; after wash it for 3 times, second antibody is prepared by using 500 μl goat anti-human fluorescent antibody for 1 hour at 37° C.; after wash it for 3 times and seal it by using 50% glycerol PBS, observe green fluorescence protein under fluorescence inverted microscope. (Only pIRES2-DsRed2-ureI plasmid transfects HEK293T cell group); set a comparison group of empty plasmid transfecting HEK293T cell group. (The muscle cell cannot be detect via immunofluorescence assay because the muscle cells are sticking to the wall; use red fluorescence sign on the transfection plasmid to calculate the transfection of the target gene indirectly.) Cell orthotopi immunohistochemistry shows that there is brown particle express at cytoplasm near membrane.

Embodiment 4

Verification on Prevention and Therapeutic Effect of DNA Vaccine 4.1 Screening of Experimental Animal Strain and Construction of Animal Model For discover which animal strain can stimulate the clinical symptoms of Hp infecting human being best, this part of experiment use I type *Helicobacter pylori* (Hp) SSI bacterial strain of Ure+, CagA+ and VacA+ to process three types of mice (BALB/c, NIH and KM) via circularly dropping feed, and detect the cell colonization, antibody level and pathological changes in 14, 39, 69, and 105 days respectively.

The result shows that Hp can keep being colonized on the gastric mucosa of rat, and stimulate Hp antibody (IgG) to stay a relative high level, wherein the bacteria colonization of BALB/c is early, the colonization rate is high, and the stomach lesion is the most obvious. Hp mainly causes the gastric mucosal bleeding, degeneration and necrosis with inflammatory response of lymphocytic infiltration, which is very similar to the Hp causing human gastropathy. Therefore, this experiment selects BALB/c rat as Hp infecting animal model to evaluate DNA vaccine.

4.2 Verification on Prevention Effects of DNA Vaccine

Set a experiment group and a comparison group, each group having 30 mice. The mice in the experiment group are injected with removing endotoxin DNA vaccine plasmid, and the comparison group are injected with empty vector plasmid. Inject again in No. 7 and 14 days after the first immunization, three times in total.

Conduct Hp infection experiment in one week after the last immunization. Take Hp cultivated by brinell agar, elute it aseptically to aseptic tube by using 0.02 mol/l Ph 7.4 PBS, and adjust the bacteria concentration to $10^9$ CFU/ml as infecting bacterial liquid. Infect two groups of mice via circularly dropping feed.

Kill the mice after the fourth week after the last feed, and separate serum and gastric mucosa. Conduct quick urease experiment on the gastric mucosa, smear directly, and perform gram stain microscopic examination. The result interpretation method is: gram-negative rod-shaped bacteria and urease test positive can be determined as Hp infection.

Protection rate=(uninfected rate/number of survivals)*100%

Infection rate=(infection rate/number of survivals)*100%

The results are shown in Table 1.

TABLE 1

| Group | Number of total mice | Number of infected mice | Number of uninfected mice | Infection rate | Protection rate |
|---|---|---|---|---|---|
| Experiment group | 30 | 6 | 24 | — | 80% |
| Comparison group | 30 | 27 | 3 | 90% | — |

4.3 Verification on Therapeutic Effects of DNA Vaccine

Set an experiment group and a comparison group, each group having 30 mice. Firstly, conduct Hp infection experiment by using above-mentioned method. Determine anti-Hp antibody titer by taking serum samples to confirm infection effect after 14 days. Take out the confirmed infected mice. The mice in the experiment group are injected with removing endotoxin DNA vaccine plasmid at multiple muscle spots, and the comparison group are injected with empty vector plasmid. Inject again in No. 7 and 14 days after the first injection, three times in total.

The treatment effectiveness evaluation by observing mice daily: the clinical symptoms of the mice at 14, 39 and 69 days after injected with recombination DNA vaccine plasmid and empty plasmid in muscle (rough hair has 0 score, symptoms disappearing has −1 score); peripheral blood Hp antibody IgG via ELISA detecting model (decreasing has −1 score, increasing and unchanged has 0 score); urease experiment (negative has −1 score, positive has 0 score); Hp colonization volume determination via bacteria cultivation colony counting (number decreasing has −1 score, increasing and unchanged has 0 score); gland inflammation of gastric tissue via pathological diagnosis (lightening has −1 score, aggravating or unchanged has 0 score); bleed (lightening has −1 score, aggravating or unchanged has 0 score); edema (lightening has −1 score, aggravating or unchanged has 0 score), atrophy (lightening has −1 score, aggravating or unchanged has 0 score); necrosis (lightening has −1 score, aggravating or unchanged has 0 score). The treatment effectiveness to each group after injected with recombination DNA vaccine plasmid in muscle is evaluated comprehensively.

Statistic analysis: the treatment effectiveness is determined according to bacteria Hp colonization volume, gastric tissue medical record, antibody IgG level, and IFN-γ variation comprehensive score. The calculation method: during the pathogenesis, the sum of the highest score in one group divided by the number of the animals is the average clinical score of this group. The Kruskal-Wallis is adopted to compare the clinical score ±SD value and peripheral blood antibody IgG and cytokine levels ±SD between the groups; when P<0.05, the Mann-Whitney U is adopted to compare between the groups.

Figure 2:
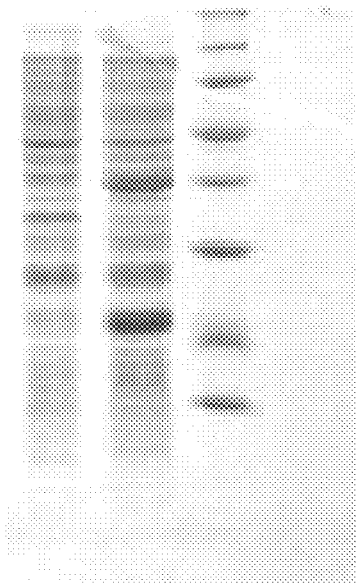
FIG. 2 is an illustrative view of induced expression of multi-target fusion polypeptide verified by SDS-PAGE.

Assume that the clinical integral score is 8, and clinical relative score is 100%. Comparing to the comparison group, after 14 days of recombinant DNA vaccine immunization, the clinical relative score of experiment group is unchanged. Comparing to the comparison group, after 39 days of DNA vaccine immunization, the clinical relative score of experiment group is 78%. Comparing to the comparison group, after 69 days oral administration of specific antibody, the clinical relative score of experiment group is 27.9%. The difference of the comparison group and experiment group after 14 days immunization has no statics value (PP>0.05), but the difference in 39 days and 69 days has statics value (P>0.01). The details are shown in FIG. 2.

TABLE 2

| Time (days) | Comparison group | Experiment group |
|---|---|---|
| 14 | 7.91 ± 0.16 | 8.02 ± 0.17 |
| 39 | 8.36 ± 0.34 | 6.50 ± 0.26 |
| 69 | 8.13 ± 0.35 | 2.20 ± 0.21 |

Note:
n = 5

Embodiment 5

Design, Construction, Verification of Prokaryotic Expression Vector of Multi-Target Fusion Polypeptide Select PET28a(+) prokaryotic expression vector and connect the synthesized DNA sequence of the encoding fusion polypeptide and the vector after EcoRI and XhoI double enzyme digestion and transform into competent cell of DH5a. Positive clone plasmid is transformed to express host strain Rosseta gami II via PCR and double enzyme digestion, and the positive clone is sent to test sequence via PCR. Prepare epitope peptide for induced expression.

Embodiment 6

Figure 3:
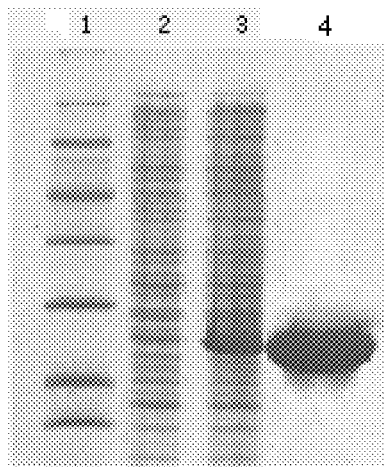
FIG. 3 is an illustrative view of purification of recombination multi-target fusion polypeptide verified by SDS-PAGE.
Figure 4:
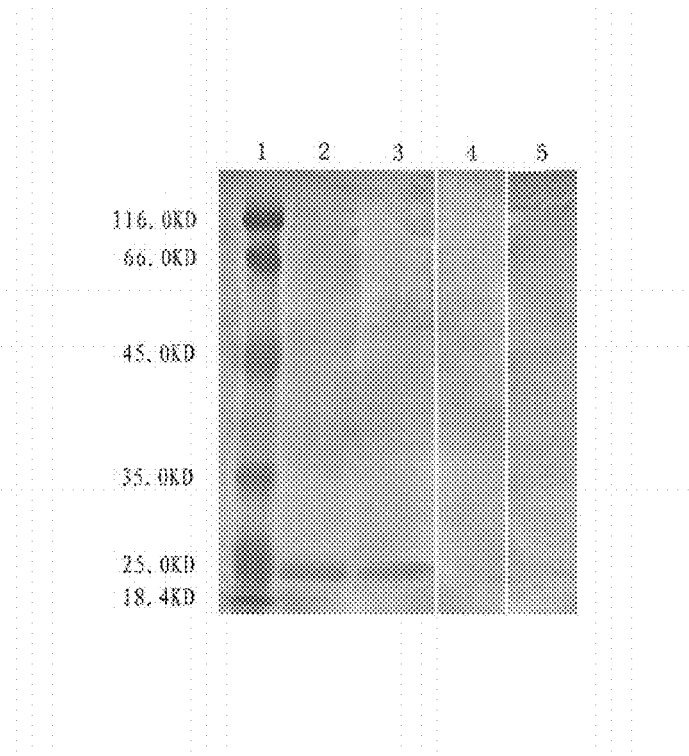
FIG. 4 is an illustrative view of specific reactionogenicity of recombination multi-target fusion polypeptide verified by Western Blot.

The Induced Expression, Purification and Westernblot Verification of Multi-Target Fusion Polypeptide Induce by using inducer IPTG according to the PET prokaryotic expression system inducing operation process. Take samples before and after inducement. The result of SDS-PAGE verification and analysis is shown in FIG. 2.
  Swin Lane 1: before expression bacteria induction;
  Swin Lane 2: after expression bacteria induction;
  Swin Lane 3: Protein MARKER;
  The results show that an obvious protein band appears at 30 KD after the inducement, which is equivalent to the predicted protein molecular weight.
  Purify the multi-target fusion polypeptide via His tag of the PET28a(+) vector. The purification result is shown in FIG. 3.
  Swin Lane 1: Protein MARKER;
  Swin Lane 2: the bacteria precipitate after ultrasonication;
  Swin Lane 3: the bacteria are supernatant after ultrasonication;
  Swin Lane 4: Ni column elution
  The result shows: the target protein is soluble in the cytoplasm, and the electrophoresis purity is above 90% after purification.
  Transfer purified multi-target fusion polypeptide to NC membrane by electroporation, and first antibody is performed to verify the immunological specificity of multi-target fusion polypeptide via anti Hp human serum and anti UreB monoclonal antibody. The results are shown in FIG. 4.
  Swin Lane 1: Protein MARKER;
  Swin Lane 2: multi-target fusion polypeptide, first antibody is antihuman Hp positive serum.
  Swin Lane 3: multi-target fusion polypeptide, first antibody is anti UreB monoclonal antibody.
  Swin Lane 4: multi-target fusion polypeptide, first antibody is normal serum.
  Swin Lane 5: empty expression bacteria splitting liquor, first antibody is anti UreB monoclonal antibody.

The results show that the reactivity of multi-target fusion polypeptide and anti Hp human serum and UreB monoclonal antibody.

Embodiment 7

Animal Immunizing Effect Verification of Multi-Target Fusion Polypeptide

Use multi-target fusion polypeptide to immunize 5 rabbits, 500 ug/per rabbit. Immunize once every 14 days after the first immunization. Take blood samples one week after each immunization, and separate serum. Cover 96-hole board with prepared multi-target fusion polypeptide, and detect serum anti recombination UreI-B titer via indirect ElISA. The titer variation is shown in Table 3.

TABLE 3

| immunizing days | 0 | 7 | 21 | 35 | 49 |
|---|---|---|---|---|---|
| anti-Hp titer | 0 | $10^2$ | $10^3$ | $10^4$ | $10^5$ |

Figure 5:
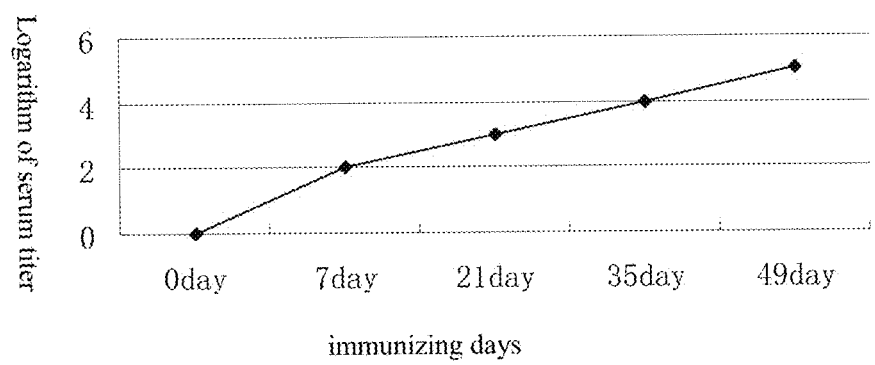
FIG. 5 is an illustrative view of specific immunogenicity after animal is immunized by recombination multi-target fusion polypeptide.

The titer variation is shown in FIG. 5 The data shows that the of multi-target fusion polypeptide has good immunogenicity and produces antibody after immunization for 7 days, and the titer rises fast.

Embodiment 8

Preparation of Specific Antibody of Anti Multi-Target Fusion Polypeptide

Kill the rabbit by taking blood in the heart when the immunizing titer is up to $10^5$, collect serum, and prepare affinity chromatography.
Couple multi-target fusion polypeptide to sepharose 4FF filler activated by CNBr. The coupling method is according to the filler explanation. After packing balance, dilute the rabbit serum to 5 times by using Loading Buffer after, and circularly make samples for 4-5 times. Elute by using elution buffer, and collect elution peak. The antibody concentration is analyzed by OD260/280, and the antibody purification is verified by SDS-PAGE. The result shows that the antibody purity is above 95%. Dialyze antibody into 10 mM PBS and concentrate it to above 2 mg/ml for further usage.

Embodiment 9

Verification on Specific Antibody of Anti Multi-Target Fusion Polypeptide Curing Hp Infection Effect Set a experiment group and a comparison group, each group having 30 mice. Firstly, conduct Hp infection experiment by using above-mentioned method. Determine anti-Hp antibody by taking serum samples to confirm infection effect after 14 days. Take out the confirmed infected mouse, administrate the experiment group anti multi-target fusion polypeptide specific antibody, and administrate the comparison group PBS buffer. Administrate daily for the 14-day course of treatment.
The treatment effectiveness evaluation by observing mice daily: the clinical symptoms of the mice at 14, 39 and 69 days after oral administration (rough hair has 0 score, symptoms disappearing has −1 score); peripheral blood Hp antibody IgG via ELISA detecting model (decreasing has −1 score, increasing and unchanged has 0 score); urease experiment (negative has −1 score, positive has 0 score); Hp colonization volume determination via bacteria cultivation colony counting (number decreasing has −1 score, increasing and unchanged has 0 score); gland inflammation of gastric tissue via pathological diagnosis (lightening has −1 score, aggravating or unchanged has 0 score); bleed (lightening has −1 score, aggravating or unchanged has 0 score); edema (lightening has −1 score, aggravating or unchanged has 0 score), atrophy (lightening has −1 score, aggravating or unchanged has 0 score); necrosis (lightening has −1 score, aggravating or unchanged has 0 score). The treatment effectiveness is evaluated comprehensively.

Statistic analysis: the treatment effectiveness is determined according to bacteria Hp colonization volume, gastric tissue medical record, antibody IgG level, and IFN-γ variation comprehensive score. The calculation method: during the pathogenesis, the sum of the highest score in one group divided by the number of the animals is the average clinical score of this group. The Kruskal-Wallis is adopted to compare the clinical score ±SD value and peripheral blood antibody IgG and cytokine levels ±SD between the groups; when $P<0.05$, the Mann-Whitney U is adopted to compare between the groups.

Assume that the clinical integral score is 8, and clinical relative score is 100%. Comparing to the comparison group, after 14 days oral administration of specific antibody, the clinical relative score of experiment group is 56%. Comparing to the comparison group, after 39 days oral administration of specific antibody, the clinical relative score of experiment group is 23%. Comparing to the comparison group, after 69 days oral administration of specific antibody, the clinical relative score of experiment group is 10%. The difference of the comparison group and experiment group after oral administration of specific antibody for 14 days, 39 days and 69 days has statics value ($P<0.01$). The details are shown in FIG. 4.

TABLE 4

| Time (days) | Comparison group | Experiment group |
|---|---|---|
| 14 | 7.61 ± 0.16 | 4.42 ± 0.17 |
| 39 | 8.56 ± 0.34 | 1.92 ± 0.26 |
| 69 | 8.83 ± 0.35 | 0.82 ± 0.21 |

Note:
n = 5

Results show that the specific antibody is very effective on oral treatment of Hp infection.

According to the above experiments, the present invention is fully realized.

What is claimed is:

1. A multi-target fusion polypeptide comprising amino acid sequence shown in SEQ ID NO:2.

2. A nucleotide sequence encoding the amino acid sequence shown in SEQ ID NO:2, wherein the nucleotide sequence encoding the amino acid sequence is multi-target recombination gene of the nucleotide sequence shown in SEQ ID NO:1.

3. A prokaryotic expression vector or eukaryotic expression vector comprising the nucleotide sequence shown in SEQ ID NO:1 as recited in claim 2.

* * * * *

SEQUENCE LISTING

<160> NUMBER OF SEQ ID NOS: 2

<210> SEQ ID NO 1
<211> LENGTH: 558
<212> TYPE: DNA
<213> ORGANISM: Helicobacter pylori

<400> SEQUENCE: 1

```
ggattaacca aagtcgatcc taaaagcacc aaaaaaggtt tggattggcg tccgtattct      60
tggtataaaa aaatgtatgg ccctaccaca ggcgataaag tgcgtttgaa aaaatctgca     120
atcaatcatg cgttagacgt tgcggacaaa tacgatgtgc aagtcgctat ccacacagac     180
actaaaaaaa gcattaaaga agatgtccag ttcgctgatt cacgtatccg ccctcaaacc     240
attgcggctg aagacacttt gcatgacatg gggattttct caatcaccag ttctgactct     300
caagcgatgg gtcgtgtggg tgaagttatc actcgtactt ggcaaacagc tgacaaaaac     360
aaaaaagaat ttggccgctt gaaagaagaa aaaggcgata acgacaactt caaaaaaccg     420
gttaaaaatt gccgtaacat cactaaaaaa gacatgcaat tcaatgacac taccgctcac     480
attgaagtca atcctgaaac ttaccatgtg ttcgtggatg gcaaagaagt cacttctaaa     540
ccagctaata aagtgagc                                                   558
```

<210> SEQ ID NO 2
<211> LENGTH: 186
<212> TYPE: PRT
<213> ORGANISM: Helicobacter pylori

<400> SEQUENCE: 2

```
Gly Leu Thr Lys Val Asp Pro Lys Ser Thr Lys Lys Gly Leu Asp Trp
1               5                   10                  15

Arg Pro Tyr Ser Trp Tyr Lys Lys Met Tyr Gly Pro Thr Thr Gly Asp
            20                  25                  30

Lys Val Arg Leu Lys Lys Ser Ala Ile Asn His Ala Leu Asp Val Ala
        35                  40                  45
```

```
Asp Lys Tyr Asp Val Gln Val Ala Ile His Thr Asp Thr Lys Lys Ser
    50                  55                  60

Ile Lys Glu Asp Val Gln Phe Ala Asp Ser Arg Ile Arg Pro Gln Thr
65              70                  75                  80

Ile Ala Ala Glu Asp Thr Leu His Asp Met Gly Ile Phe Ser Ile Thr
            85                  90                  95

Ser Ser Asp Ser Gln Ala Met Gly Arg Val Gly Glu Val Ile Thr Arg
            100                 105                 110

Thr Trp Gln Thr Ala Asp Lys Asn Lys Lys Glu Phe Gly Arg Leu Lys
        115                 120                 125

Glu Glu Lys Gly Asp Asn Asp Asn Phe Lys Lys Pro Val Lys Asn Cys
    130                 135                 140

Arg Asn Ile Thr Lys Lys Asp Met Gln Phe Asn Asp Thr Thr Ala His
145                 150                 155                 160

Ile Glu Val Asn Pro Glu Thr Tyr His Val Phe Val Asp Gly Lys Glu
                165                 170                 175

Val Thr Ser Lys Pro Ala Asn Lys Val Ser
            180                 185
```